United States Patent [19]

Berg et al.

[11] Patent Number: 4,710,274

[45] Date of Patent: Dec. 1, 1987

[54] SEPARATION OF ETHANOL FROM ISOPROPANOL BY EXTRACTIVE DISTILLATION

[76] Inventors: Lloyd Berg, 1314 S. 3rd Ave., Bozeman, Mont. 59715; Mark G. Vosburgh, 4670 - 23rd Ave., Missoula, Mont. 59803

[21] Appl. No.: 892,288

[22] Filed: Aug. 4, 1986

Related U.S. Application Data

[63] Continuation-in-part of Ser. No. 757,318, Jul. 19, 1985, abandoned.

[51] Int. Cl.[4] .......................... B01D 3/40; C07C 29/84
[52] U.S. Cl. ........................................ 203/51; 203/60; 203/61; 203/65; 568/913
[58] Field of Search .................. 203/51, 60, 61, 57, 203/63, 65; 568/913, 918

[56] References Cited

U.S. PATENT DOCUMENTS

| | | | |
|---|---|---|---|
| 2,551,584 | 5/1951 | Carlson et al. | 203/51 |
| 2,552,412 | 5/1951 | Drout et al. | 203/84 |
| 2,559,519 | 7/1951 | Smith et al. | 203/64 |
| 2,559,520 | 7/1951 | Smith et al. | 203/64 |
| 2,570,205 | 10/1951 | Carlson et al. | 203/58 |
| 2,575,243 | 11/1951 | Carlson et al. | 203/60 |
| 2,591,712 | 4/1952 | Morrell et al. | 203/84 |
| 2,591,713 | 4/1952 | Morrell et al. | 203/84 |
| 2,706,707 | 4/1955 | Morrell et al. | 203/57 |

*Primary Examiner*—Wilbur Bascomb

[57] ABSTRACT

Ethanol and isopropanol cannot be separated from each other by distillation because of the proximity of their boiling points. Ethanol can be readily separated from isopropanol by using extractive distillation in which the extractive agent is a higher boiling oxygenated organic compound or a mixture of two or more of these. Typical examples of effective agents are: methyl salicylate; salicylic acid and hexahydrophthalic anhydride; salicylic acid, hexahydrophthalic anhydride and methyl benzoate.

5 Claims, No Drawings

SEPARATION OF ETHANOL FROM ISOPROPANOL BY EXTRACTIVE DISTILLATION

This is a continuation in-part of application Ser. No. 06/757,318 filed July 19, 1985, and now abandoned.

FIELD OF THE INVENTION

This invention relates to a method for separating ethanol from isopropanol using certain higher boiling liquids as the extractive agent in extractive distillation.

DESCRIPTION OF PRIOR ART

Extractive distillation is the method of separating close boiling compounds from each other by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. The extractive agent should boil higher than any of the close boiling liquids being separated and not form minimum azeotropes with them. Usually the extractive agent is introduced a few plates from the top of the column to insure that none of the extractive agent is carried over with the lowest boiling component. This usually requires that the extractive agent boil about twenty Centigrade degrees or more higher than the lowest boiling component.

At the bottom of a continuous column, the less volatile components of the close boiling mixtures and the extractive agent are continuously removed from the column. The usual methods of separation of these two components are the use of another rectification column, cooling and phase separation, or solvent extraction.

Ethanol and isopropanol are the two most widely used alcohols in commerce today. When they are used as solvents, they frequently end up as a mixture of solvents. Whenever practical, it is mandatory to recover the solvent and re-use it.

Ethanol and isopropanol are both manufactured by the hydration of the corresponding olefin, ethylene for ethanol and propylene for isopropanol. At present the ethylene and propylene are separated to high purity before reaction with sulfuric acid and water to make the alcohol to avoid the formation of a mixture of these two alcohols in the reaction product. The usual way of recovering liquid components is by distillation in a multiplate rectification column. Ethanol boils at 78.4° C. isopropanol at 82.4° C. and these two have a relative volatility of 1.09, making it virtually impossible to separate these two by this method.

Extractive distillation would be an attractive method of effecting the separation of ethanol from isopropanol if agents can be found that (1) will alter the relative volatility between ethanol and isopropanol, (2) form no azeotrope with ethanol or isopropanol and (3) are easy to recover from isopropanol, that is boil sufficiently above isopropanol to make the separation by rectification possible with only a few theoretical plates.

Extractive distillation typically requires the addition of an equal amount to twice as much extractive agent as the ethanol - isopropanol on each plate of the rectification column. The extractive agent should be heated to about the same temperature as the plate into which it is introduced. Thus extractive distillation imposes an additional heat requirement on the column as well as somewhat larger plates. However this is less than the increase occasioned by the additional agents required in azeotropic distillation.

Another consideration in the selection of the extractive distillation agent is its recovery from the bottoms product. The usual method is by rectification in another column. In order to keep the cost of this operation to a minimum, an appreciable boiling point difference between the compound being separated and the extractive agent is desirable. We recommend twenty Centigrade degrees or more difference. It is also desirable that the extractive agent be miscible with the isopropanol otherwise it will form a two phase azeotrope with it and some other method of separation will have to be employed.

C. S. Carlson & P. V. Smith, U.S. Pat. No. 2,570,205 described an extractive distillation process to separate ethanol from isopropanol using sulfolane as the agent. C. E. Morrell, U.S. Pat. No. 2,706,707 uses the salts of aromatic ring organic compounds as the extractive distillation agents for this separation.

OBJECTIVE OF THE INVENTION

The object of this invention is to provide a process or method of extractive distillation that will enhance the relative volatility of ethanol from isopropanol in their separation in a rectification column. It is a further objective of this invention to identify organic compounds which are stable, can be separated from isopropanol by rectification with relatively few plates and can be recycled to the extractive distillation column and re-used with little decomposition.

SUMMARY OF THE INVENTION

The objects of this invention are provided by a process for separating ethanol from isopropanol which entails the use of cetain oxygenated organic compounds as the agent in extractive distillation.

DETAILED DESCRIPTION OF THE INVENTION

We have discovered that certain oxygenated organic compounds, some individually but principally as mixtures, will effectiely enhance the relative volatility between ethanol and isopropanol and permit the separation of pure ethanol from isopropanol by rectification when employed as the agent in extractive distillation. Table 1 lists methyl benzoate, its mixtures and approximate proportions that we have found to be effective. Table 2 is a similar listing for methyl p-hydroxybenzoate. Table 3 lists a few otherwise unclassified benzoates. The data in Tables 1, 2 and 3 were obtained in a vapor liquid equilibrium still. In each case the starting material was the 50–50% ethanol—isopropanol mixture. The ratios are the parts of extractive agent used per part of ethanol - isopropanol mixture. The relative volatilities are listed for each of the two ratios employed.

The compounds that are effective as extractive distillation agents when used alone are methyl benzoate, methyl salicylate and ethyl salicylate. The compounds which are effective when used in mixtures of two or more components are benzoic acid, cinnamic acid, salicylic acid, phenyl salicylate, benzyl benzoate, methyl p-hydroxy benzoate, hexahydrophthalic anhydride, dipropylene glycol dibenzoate, trimellitic anhydride, methyl hexahydrophthalic anhydride, phthalic anhydride and maleic anhydride. The ratios in Tables 1, 2 and 3 are the parts of extractive agent used per part of ethanol—isopropanol mixture. The two relative volatilities correspond to the two different ratios. For example in Table 3, one part of methyl salicylate with one part of of ethanol—isopropanol mixture gives a relative volatility of 1.23, 6/5 parts of methyl salicylate gives 1.21. One half part of hexahydrophthalic anhydride mixed with one half part of salicylic acid with one part of ethanol-isopropanol mixture gives a relative volatility of 1.35, 3/5 parts of hexahydrophthalic anhydride plus 3/5 parts of salicylic acid gives 1.42. One third parts of salicylic acid plus 1/3 parts of phthalic anhydride plus ⅓ parts of hexahydrophthalic anhydride mixed with one part of ethanol - isopropanol mixture gives a relative volatility of 1.47, with 2/5 parts, these three give 1.44.

In every example in Tables 1, 2 and 3 the starting material is a 50-50% mixture of ethanol—isopropanol which possesses a relative volatility of 1.09.

TABLE 1

Extractive Distillation Agents Which Contain Methyl Benzoate.

| Compounds | Ratios | | Relative Volatilities | |
|---|---|---|---|---|
| None | — | | 1.09 | |
| Methyl benzoate | 1 | 6/5 | 1.27 | 1.17 |
| Methyl benzoate, Cinnamic acid | (½)² | (3/5)² | 1.18 | 1.25 |
| Methyl benzoate, Phthalic anhydride | " | " | 1.24 | 1.26 |
| Methyl benzoate, Ethyl salicylate | " | " | 1.26 | 1.20 |
| Methyl benzoate, Phenyl salicylate | " | " | 1.18 | 1.34 |
| Methyl benzoate, Salicylic acid | " | " | 1.22 | 1.31 |
| Methyl benzoate, Trimellitic anhydride (TMA) | " | " | 1.29 | 1.32 |
| MeBenz., Methyl p-OH benzoate, Cinnamic acid | (⅓)³ | (2/5)³ | 1.27 | 1.22 |
| MeBenz., Methyl p-OH benzoate, TMA | " | " | 1.18 | 1.21 |
| MeBenz., Methyl hexahydrophthalic anh., Cinnamic acid | " | " | 1.26 | 1.28 |
| MeBenz., Methyl hexahydrophthalic anh., Salicylic acid | " | " | 1.40 | 1.42 |
| MeBenz., Methyl hexahydrophthalic anh., TMA | " | " | 1.25 | 1.23 |
| MeBenz., TMA, Ethyl salicylate | " | " | 1.29 | 1.32 |
| MeBenz., TMA, Phenyl salicylate | " | " | 1.26 | 1.22 |
| MeBenz., TMA, Phthalic anhydride | " | " | 1.28 | 1.28 |
| MeBenz., TMA, Salicylic acid | " | " | 1.51 | 1.48 |
| MeBenz., Benzoic acid, Methyl hexahydrophthalic anh. | " | " | 1.28 | 1.31 |
| MeBenz., MeHHPh anh., Phthalic anh., Cinnamic acid | (¼)⁴ | (⅓)⁴ | 1.45 | 1.41 |
| MeBenz., MeHHPh anh., Cinnamic acid, Me p-OH benzoate | " | " | 1.18 | 1.20 |
| MeBenz., MeHHPh anh., Benzoic acid, Phthalic anh. | " | " | 1.20 | 1.38 |
| MeBenz., TMA, HexahydroPh. anh., DiPr glycol dibenzoate | " | " | 1.10 | 1.24 |

TABLE 2

Extractive Distillation Agents Which Contain Methyl p-OH Benzoate.

| Compounds | Ratios | | Relative Volatilities | |
|---|---|---|---|---|
| Methyl p-hydroxybenzoate (MPHB), TMA | (½)² | (3/5)² | 1.39 | 1.29 |
| MPHB, Salicylic acid | " | " | 1.19 | 1.24 |
| MPHB, Salicylic acid, Maleic anhydride | (⅓)³ | (2/5)³ | 1.25 | 1.30 |
| MPHB, Ethyl salicylate, HexahydroPh anh. | " | " | 1.25 | 1.21 |
| MPHB, TMA, Benzyl benzoate | " | " | 1.24 | 1.25 |
| MPHB, TMA, Ethyl salicylate | " | " | 1.25 | 1.33 |
| MPHB, TMA, HexahydroPh anh. | " | " | 1.50 | 1.34 |
| MPHB, TMA, Maleic anhydride | " | " | 1.24 | 1.17 |
| MPHB, TMA, Phthalic anhydride | " | " | 1.39 | 1.29 |

TABLE 3

Extractive Distillation Agents Which Contain Benzoates.

| Compounds | Ratios | | Relative Volatilities | |
|---|---|---|---|---|
| Methyl o-hydroxybenzoate (Methyl salicylate) | 1 | 6/5 | 1.23 | 1.21 |
| Ethyl o-hydroxybenzoate (Ethyl salicylate) | " | " | 1.22 | 1.19 |
| Methyl o-OH benzoate, Cinnamic acid | (½)² | (3/5)² | 1.22 | 1.21 |
| Ethyl o-OH benzoate, HexahydroPh anh. | " | " | 1.31 | 1.20 |
| Ethyl o-OH benzoate, TMA | " | " | 1.28 | 1.29 |
| Benzyl benzoate, TMA | " | " | 1.31 | 1.31 |
| Benzoic acid, Methyl hexahydroPh anh. | " | " | 1.25 | 1.25 |
| o-Hydroxybenzoic acid (Salicylic acid), TMA | " | " | 1.21 | 1.28 |
| o-Hydroxybenzoic acid, HexahydroPh anh. | " | " | 1.35 | 1.42 |
| o-Hydroxybenzoic acid, Maleic anhydride | " | " | 1.30 | 1.36 |
| o-Hydroxybenzoic acid, TMA, HexahydroPh Anh. | (⅓)³ | (2/5)³ | 1.43 | 1.43 |
| o-Hydroxybenzoic acid, TMA, Maleic anhydride | " | " | 1.46 | 1.47 |
| o-Hydroxy benzoic acid, Phthalic anh., HexahydroPh Anh. | " | " | 1.47 | 1.44 |
| Dipropylene glycol dibenzoate (DPGDB), TMA, Maleic anh. | " | " | 1.31 | 1.30 |
| DPGDB, TMA, HexahydroPh. anh. | " | " | 1.26 | 1.34 |
| DPGDB, Salicylic acid, HexahydroPh anh. | " | " | 1.19 | 1.24 |

TABLE 4

Data From Runs Made In Rectification Column.

| Agent | Time min. | Stillpot Temp. °C | | Overhead Temp. When Sampling | Weight % Ethanol | | Relative Volatility |
|---|---|---|---|---|---|---|---|
| | | At Start | Sampling | | Overhead | Bottoms | |

TABLE 4-continued

Data From Runs Made In Rectification Column.

| | | | | | | | |
|---|---|---|---|---|---|---|---|
| None | 60 | 79.0 | 79.8 | 74.8 | 62.0 | 52.1 | 1.09 |
| None | 90 | 79.0 | 79.4 | 74.8 | 61.8 | 52.9 | 1.08 |
| None | 120 | 79.0 | 80.8 | 75.0 | 61.3 | 51.0 | 1.10 |
| | | | | | | | 1.09 average |
| Methyl benzoate | 60 | 80.0 | 91.6 | 75.6 | 72.6 | 52.4 | 1.22 |
| Methyl benzoate | 90 | 80.0 | 94.8 | 76.2 | 73.5 | 50.7 | 1.25 |
| Methyl benzoate | 120 | 80.0 | 100.6 | 76.0 | 72.2 | 47.1 | 1.27 |
| | | | | | | | 1.25 average |
| Methyl benzoate, reclaimed + Salicylic acid | 60 | 81.0 | 93.2 | 76.2 | 70.0 | 50.4 | 1.20 |
| Methyl benzoate, reclaimed + Salicylic acid | 90 | 81.0 | 99.4 | 75.8 | 67.9 | 49.5 | 1.19 |
| Methyl benzoate, reclaimed + Salicylic acid | 120 | 81.0 | 108.2 | 76.2 | 71.3 | 44.9 | 1.28 |
| | | | | | | | 1.22 average |

Notes for Table 5

| Agent | Feed, Wt. % EtOH | Agent Rate of Flow, ml/min | Boilup Rate ml/min. | Agent Temp, °C. | Composition of Agent, Wt. % |
|---|---|---|---|---|---|
| None | 50 | 0 | 10–20 | — | — |
| Methyl benzoate | 50 | 20 | 10–20 | 70–80 | 100% Me benzoate |
| Me benzoate (reclaimed) + Salicylic acid | 50 | 20 | 10–20 | 75–80 | 14% Sal. acid, 86% Me benzoate |

Two of the compounds listed Table 1 and whose relative volatility had been determined in the vapor-liquid equilibrium still, were then evaluated in a glass perforated plate rectifion column possessing 4.5 theoretical plates. The results are listed in Table 4. The ethanol—isoprpanol mixture used contained about 50% ethanol. The first run is with no extractive agent and with 400 grams of about 50% mixture in the stillpot. After 60 minutes of operation, the separation is that in accordance with a relative volatility of 1.09. Further operation for another 60 minutes does not change the relative volatility. The second run is with methyl benzoate as the extractive agent and here a relative volatility of 1.25 is obtained. This compares with the 1.27 and 1.17 shown for methyl benzoate in Table 1, the data for which was obtained in the vapor-liquid equilibrium still. The third run is with a mixture comprising 86% reclaimed methyl benzoate, 14% salicylic acid. This agent gives a relative volatility of 1.22 which is the same as this mixture gave in Table 1.

THE USEFULNESS OF THE INVENTION

The usefulness or utility of this invention can be demonstrated by referring to the data presented in Tables 1, 2, 3 and 4. All of the successful extractive distillation agents show that ethanol can be removed from isopropanol by means of distillation in a rectification column and that the ease of separation as measured by relative volatility is considerable. Without these extractive distillation agents, virtually no improvement will occur in the rectification column. The data also show that the most attractive agents will operate at a boilup rate low enough to make this a useful and efficient method of recovering high purity ethanol from any mixture with isopropanol. The stability of the compounds used and the boiling point difference is such that complete recovery and recycle is obtainable by a simple distillation and the amount required for make-up is small.

WORKING EXAMPLES

Example 1: Twenty-five grams of ethanol, 25 grams of isopropanol and fifty grams of methyl salicylate were charged to an Othmer type glass vapor-liquid equilibrium still and refluxed for seven hours. Analysis of the vapor and liquid by gas chromatography gave a vapor composition of 57.8% ethanol, 42.2% isopropanol; a liquid composition of 52.7% ethanol, 47.3% isopropanol. This indicates a relative volatility of 1.23. Ten grams of methyl salicylate were added and refluxing continued for another four hours. Analysis indicated a vapor composition of 57.2% ethanol, 42.8% isopropanol; a liquid composition of 52.5% ethanol, 47.5% isopropanol which is a relative volatility of 1.21.

EXAMPLE 2

Fifty grams of the ethanol-isopropanol mixture, 25 grams of salicylic acid and 25 grams of hexahydrophthalic anhydride were charged to the vapor-liquid equilibrium still and refluxed for 16 hours. Analysis indicated a vapor composition of 57.4% ethanol, 42.6% isopropanol, a liquid composition of 50% ethanol, 50% isopropanol which is a relative volatility of 1.35. Five grams of salicylic acid and five grams of hexahydrophthalic anhydride were added and refluxing continued for another eight hours. Analysis indicated a vapor composition of 55.1% ethanol, 44.9% isopropanol; a liquid composition of 46.3% ethanol, 53.7% isopropanol which is a relative volatility of 1.42.

EXAMPLE 3

Fifty gram of the ethanol - isopropanol mixture, 17 grams of salicylic acid, 17 grams of hexahydrophthalic anhydride and 17 grams of methyl benzoate were charged to the vapor-liquid equilibrium still and refluxed for 17 hours. Analysis indicated a vapor composition of 57.1% ethanol, 42.9% isopropanol; a liquid composition of 48.7% ethanol, 51.3% isopropanol which is a relative volty of 1.40. Three grams each of salicylic acid, hexahydrophthalic anhydride and methyl benzoate were added and refluxing continued for another ten hours. Analysis indicated a vapor composition of 54.7% ethanol, 45.3% isopropanol and a liquid composition of 45.9% ethanol, 54.1% isopropanol which is relative volatility of 1.42.

EXAMPLE 4

A glass perforated plate rectification column was calibrated with ethylbenzene and p-xylene which possesses a relative volatility of 1.06 and found to have 4.5 theoretical plates. A solution of 200 grams of ethanol and 200 grams of isopropanol was placed in the stillpot and heated. When refluxing began, an extractive agent consisting of pure methyl benzoate was pumped into the column at a rate of 20 ml/min. The temperature of the extractive agent as it entered the column was 70°–80° C. After establishing the feed rate of the extractive agent, the heat input to the ethanol - isopropanol in the stillpot was adjusted to give a reflux rate of 10–20 ml/min. After one hour of operation, overhead and bottoms samples of approximately two ml. were collected and analysed using gas chromatography. The overhead analysis was 72.6% ethanol, 27.4% isopropanol. The bottoms analysis was 52.4% ethanol, 47.6% isopropanol. Using these compositions in the Fenske equation, with the number of theoretical plates in the column being 4.5, gave an average relative volatility of 1.22 for each theoretical plate. After 1.5 hours of total operating time, the overhead and bottoms samples were again taken and analysed. The overhead composition was 73.5% ethanol, 26.5% isopropanol and the bottoms composition was 50.7% ethanol, 49.3% isopropanol. This gave an average relative volatility of 1.25 for each theoretical plate. After two hours of total operating time, the overhead and bottoms samples were again taken and analysed. The overhead composition was 72.2% ethanol, 27.8% isopropanol and the bottoms composition was 47.1% ethanol, 52.9% isopropanol. This gave an average relative volatility of 1.27 for each theoretical plate.

Example 5

A solution of 200 grams of ethanol and 200 grams of isopropanol was placed in the stillpot of the same column used in example 4 and heat applied. When refluxing began, an extractive agent comprising 86% methyl benzoate, 14% salicylic acid was fed to the top of the column at a feed rate of 20 ml/min. and a temperature of 75°–80° C. After establishing the feed rate of the extractive agent, the heat input to the ethanol - isopropanol in the stillpot was adjusted to give a total reflux rate of 10–20 ml/min. Having established the reflux rate, the column was allowed to operate for one hour. After one hour of steady operation, overhead and bottoms samples of approximately two ml. were collected and analysed by gas chromatography. The overhead analysis was 70% ethanol, 30% isopropanol, the bottoms analysis was 50.4% ethanol, 49.6% isopropanol. Using these compositions in the Fenske equation with the number of theoretical plates in the column being 4.5, gave an average relative volatility of 1.20 for each theoretical plate. After 1.5 hours of total operation, the overhead composition was 67.9% ethanol, 32.1% isopropanol and the bottoms composition was 49.5% ethanol, 50.5% isopropanol. This gave an average relative volatility of 1.19 for each theoretical plate. After two hours of total operation, the overhead composition was 71.3% ethanol, 28.7% isopropanol and the bottoms composition was 44.9% ethanol, 55.1% isopropanol. This gave an average relative volatility of 1.28 for each theoretical plate.

What is claimed is:

1. A method for recovering ethanol from a mixture of ethanol and isopropanol which comprises distilling a mixture of ethanol and isopropanol in a rectification column in the presence of about one to two parts of extractive agent per part of ethanol—isopropanol mixture, recovering ethanol as overhead product and obtaining the extractive agent and isopropanol from the stillpot, the extractive agent comprises a benzoate containing from eight to nine carbon atoms.

2. The method of claim 1 in which the extractive agent is methyl benzoate.

3. The method of claim 1 in which the extractive agent is methyl o-hydroxybenzoate.

4. The method of claim 1 in which the extractive agent is ethyl o-hydroxybenzoate.

5. A method for recovering ethanol from a mixture of ethanol and isopropanol which comprises distilling a mixture of ethanol and isopropanol in a rectification column in the presence of about one to two parts of extractive agent per part of ethanol - isopropanol mixture, recovering ethanol as overhead product and obtaining the extractive agent and isopropanol from the stillpot, the extractive agent comprises a benzoate containing from seven to twenty-six carbon atoms and at least one different material from the group consisting of benzoic acid, cinnamic acid, salicylic acid, phenyl salicylate, benzyl benzoate, methyl p-hydroxybenzoate, hexahydrophthalic anhydride, dipropylene glycol dibenzoate, trimellitic anhydride, methyl hexahydrophthalic anhydride, phthalic anhydride and maleic anhydride.

* * * * *